United States Patent
Hickmann et al.

(10) Patent No.: US 11,091,424 B2
(45) Date of Patent: Aug. 17, 2021

(54) PREPARATION OF ACETATE COMPOUNDS VIA A KETENE COMPOUND

(71) Applicant: BASF SE, Ludwigshafen am Rhein (DE)

(72) Inventors: Volker Hickmann, Ludwigshafen am Rhein (DE); Sumana Roy, Lampertheim (DE); Dominik Herbrecht, Ludwigshafen am Rhein (DE); Michael Acker, St. Leon-Rot (DE); Wolfgang Krause, Lampertheim (DE); Ralf Boehling, Ludwigshafen am Rhein (DE); Timon Stork, Kuantan (MY); Stefan Ruedenauer, Lampertheim (DE); Ralf Pelzer, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/955,121

(22) PCT Filed: Dec. 17, 2018

(86) PCT No.: PCT/EP2018/085118
§ 371 (c)(1),
(2) Date: Jun. 18, 2020

(87) PCT Pub. No.: WO2019/121453
PCT Pub. Date: Jun. 27, 2019

(65) Prior Publication Data
US 2020/0308094 A1    Oct. 1, 2020

(30) Foreign Application Priority Data
Dec. 18, 2017  (EP) .................................... 17207942

(51) Int. Cl.
*C07C 67/46* (2006.01)
*C07C 69/14* (2006.01)
*C07C 69/157* (2006.01)
*C07C 69/145* (2006.01)

(52) U.S. Cl.
CPC ............ *C07C 67/46* (2013.01); *C07C 69/157* (2013.01); *C07B 2200/07* (2013.01); *C07C 69/145* (2013.01); *C07C 2601/14* (2017.05)

(58) Field of Classification Search
CPC ...... C07C 67/46; C07C 69/145; C07C 69/157; C07C 2601/14
See application file for complete search history.

(56) References Cited

U.S. PATENT DOCUMENTS

| | | | |
|---|---|---|---|
| 2,685,598 A * | 8/1954 | Caldwell ................. | C07C 69/14 560/261 |
| 3,017,429 A | 1/1962 | Nayler | |
| 5,840,962 A | 11/1998 | Cohen et al. | |
| 6,156,926 A | 12/2000 | Aquila et al. | |
| 6,657,075 B2 * | 12/2003 | Williams ................. | C07C 67/46 560/231 |
| 2019/0169108 A1 | 6/2019 | Hickmann et al. | |
| 2020/0190014 A1 | 6/2020 | Hickmann et al. | |

FOREIGN PATENT DOCUMENTS

| | | | |
|---|---|---|---|
| DE | 1147937 B | 5/1963 | |
| DE | 1643714 B1 | 4/1971 | |
| EP | 0949239 A1 | 10/1999 | |
| GB | 878680 A | 10/1961 | |
| GB | 1262508 A * | 2/1972 | ............. C07C 67/46 |
| WO | WO-2010019730 A1 | 2/2010 | |
| WO | WO-2018024820 A1 | 2/2018 | |
| WO | 2018/206415 A1 | 11/2018 | |

OTHER PUBLICATIONS

Rice, F. O., et al., Ketene. I. Preparation and Reactions, Journal of the American Chemical Society, vol. 56, pp. 1760-1765 (Year: 1934).*
International Search Report for PCT/EP2018/085118 dated Mar. 18, 2019.
Written Opinion of the International Searching Authority for PCT/EP2018/085118 dated Mar. 18, 2019.
Chemiker Zeitung, [The Chemists Journal], vol. 97, No. 2, pp. 67-73.
Hurd, C. D., "Ketene", Organic Syntheses, Coll. vol. 1, p. 330 (1941); vol. 4, p. 39 (1925), 4 pages.
International Preliminary Report on Patentability received for PCT Patent Application No. PCT/EP2018/085118, dated Jul. 2, 2020, 7 pages.
Libo et al., "Synthesis of New Fragrance—Coranol and Its Acetate", Fine Chemicals, vol. 26, No. 12, Dec. 2009, 1211-1214.

* cited by examiner

*Primary Examiner* — Yate' K Cutliff
(74) *Attorney, Agent, or Firm* — Faegre Drinker Biddle & Reath LLP

(57) ABSTRACT

The present invention relates to a method for preparing acetate compounds using ketene.

17 Claims, No Drawings

PREPARATION OF ACETATE COMPOUNDS VIA A KETENE COMPOUND

CROSS-REFERENCE TO RELATED APPLICATIONS

This application is a national stage application (under 35 U.S.C. § 371) of PCT/EP2018/085118, filed Dec. 17, 2018, which claims benefit of European Application No. 17207942.8, filed Dec. 18, 2017, both of which are incorporated herein by reference in their entirety.

The present invention relates to a method for preparing acetate compounds using ketene.

BACKGROUND OF THE INVENTION

To prepare consumer goods and consumables having certain organoleptic properties, that is products having advantageous odor (olfactory) or flavor (gustatory) properties, a large number of aroma chemicals (fragrances and flavorings) are available for the exceptionally diverse fields of application of these substances. In this regard, there is a constant demand for novel substances and aroma chemicals and for novel improved preparation methods which enable the provision of individual aroma chemicals with, for example, higher efficiency or in higher purity.

It is known that esters of higher alcohols may be prepared by reacting these with carbonyl halides or with carboxylic anhydrides. A disadvantage of the reaction with carbonyl halides is that hydrohalic acids are formed in the reaction thereof, which generally lead to problems of corrosion, and elimination of water in the case of tertiary alcohols and thereby causing numerous polymerizations. The disadvantage in the reaction with carboxylic anhydrides is that equimolar amounts of the corresponding carboxylic acid are formed in the reaction mixture, which must be removed in the work-up and the reuse thereof can be technically complex.

It is further known that acetic acid esters may be prepared by reacting hydroxyl group-containing compounds with ketene. Various catalysts may be used for the reaction of hydroxyl group-containing compounds with ketene, e.g. Brønsted acids such as sulfuric acid, p-toluenesulfonic acid, phosphoric acid, potassium hydrogen sulfate or Lewis acids such as boron trifluoride or boron trifluoride etherate. However, various disadvantages have also been described for the catalyzed reaction of ketenes. For instance, acidic catalysts may cause corrosion in metal apparatuses or lead to the undesired formation of resin-like impurities. In addition, it can often be difficult to remove them again from the reaction mixture.

Methods and devices for preparing ketene are described, for example, in Organic Syntheses, Coll. Vol. 1, p. 330 (1941) and Vol. 4, p. 39 (1925) and in the Chemiker Zeitung [The Chemists Journal] 97, No. 2, pages 67 to 73 (1979).

EP 0949239 A1 describes a method for preparing linalyl acetate by reacting linalool with ketene in the presence of a zinc salt as catalyst.

DE 1643714 describes a method for preparing acetic acid esters by reacting an alcohol in the presence of certain catalysts, such as oxides of Cu(I), Bi(III), Zr(IV), Va(V), Zn(II), Mg(II), Zn(II), Co(III), Ca(II), In(III), Fe(III), Si(IV), A(III) or Cr(III).

Ruan Libo et al., Fine Chemicals, 26, 12, 2009, pp. 1211-1214, describes the synthesis of 2-acetoxy-2-methyl-4-cyclohexylbutane by reacting 2-methyl-4-cyclohexylbutan-2-ol with acetic anhydride in the presence of p-toluenesulfonyl chloride as catalyst.

WO 2010/019730 describes the use of I-menthol (1R,2S, 5R configuration) as precursor of neomenthol. In this case, I-menthol is reacted with acetic acid in the presence of diethyl azodicarboxylate and triphenylphosphine. The acetate compound 2-isopropyl-5-methylcyclohexyl acetate is obtained as intermediate compound.

The unpublished EP 17177666.9 describes a method for preparing 2,3,7-trimethyloct-6-enyl acetate and 3,7-dimethyl-2-methyleneoct-6-enyl acetate and derivatives thereof.

WO 2018/024820 describes a method for preparing 1-hydroxymethyl-1,2,2,6-tetramethylcyclohexane and derivatives thereof.

U.S. Pat. No. 3,017,429, GB 878680 and DE 1147937 describe methods for preparing linalyl acetate by reacting linalool with a ketene in the presence of an acidic esterification catalyst, such as p-Toluenesulfonic acid or sulphuric acid.

U.S. Pat. No. 5,840,962 describes a general method for preparing acetate compounds by reacting alcohols with a ketene, also in the presence of acidic esterification catalysts.

Aroma substances and fragrances have a high profile of requirements. Even minimal by-products may negatively impact the quality of the aroma substance or fragrance. Moreover, methods for preparing aroma substances and fragrances which only comprise few method steps and require less feedstocks are desirable for environmental reasons.

The object of the present invention is to provide a method for preparing acetate compounds which have the advantages mentioned above over the prior art. It has now been found, surprisingly, that this object is achieved by the method according to the invention.

Surprisingly, it has been found that acetate compounds can be prepared in a simple manner by reacting the corresponding alcohol precursors with ketene affording very high yields and at the same time high purity. By way of preference, the acetate compounds can be prepared in the absence of catalysts. This has the advantage that the reaction mixture does not have to be extracted after completion of the reaction. Consequently, the preparation time is considerably shortened. By omitting the extraction step, additional wastewater can be eliminated. Surprisingly, it was also shown that by carrying out the reaction without catalyst, the crude product is completely clear. In the case of highly colored crude products, which is often the case in the reaction mixture in the presence of catalysts, there is always a certain risk that the color is not completely removed in the subsequent distillation and as a result the quality of the aroma substance may be impaired. Thus, preferred acetate compounds, which are also suitable as aroma substances, having higher purity and therefore improved fragrance quality can be achieved than with known methods from the prior art.

SUMMARY OF THE INVENTION

The invention relates to a method for preparing acetate compounds of the formula (I) comprising the steps of

a) providing at least one compound of the formula (II)

 (II)

b) reacting the compound of the formula (II) with a ketene of the formula (III)

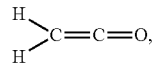 (III)

to obtain compounds of the formula (I), where $R^1$ is a heteroatom-free $C_8$-$C_{12}$-hydrocarbon radical, with the proviso that the compounds 1-acetoxymethyl-1,2,2,6-tetramethylcyclohexane and compounds of the formula (A)

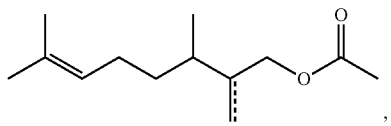 (A)

where $=\!=$ is a single or double bond, are excluded and where the compound of the general formula (II) is subjected to a reaction with a ketene (III) in the absence of an added catalyst.

Another subject-matter of the invention is a method for preparing acetate compounds of the formula (I),

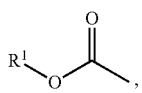 (I)

comprising the steps of
a) providing at least one compound of the formula (II)

 (II)

b) reacting the compound of formula (II) with a ketene of the formula (III)

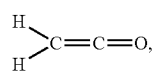 (III)

to obtain compounds of the formula (I), where $R^1$ is a heteroatom-free $C_8$-$C_{12}$-hydrocarbon radical, with the proviso that the compounds 1-acetoxymethyl-1,2,2,6-tetramethylcyclohexane and compounds of the formula (A)

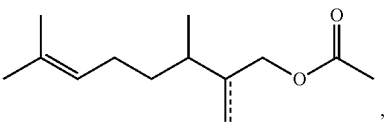 (A)

where $=\!=$ is a single or double bond are excluded or the compound 3,7-dimethyl-1,6-octadiene-3-yl-acetate (linalyl acetate) of the formula (B)

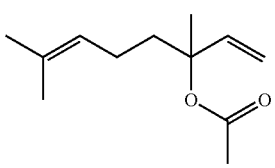 (B)

is also excluded, if the compound of the general formula (II) is subjected to a reaction with a ketene (III) in the presence of an added catalyst.

Another subject-matter of the invention is a method for preparing acetate compounds of the formula (I),

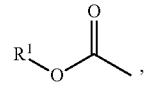 (I)

a) providing at least one compound of the formula (II)

$R^1$—OH (II)

b) reacting the compound of formula (II) with a ketene of the formula (III)

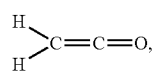 (III)

to obtain compounds of the formula (I), where $R^1$ is a heteroatom-free $C_8$-$C_{12}$-hydrocarbon radical, with the proviso that the compounds 1-acetoxymethyl-1,2,2,6-tetramethylcyclohexane and compounds of the formula (A)

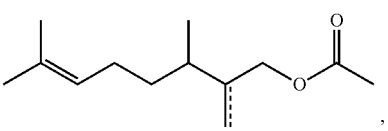 (A)

where $=\!=$ is a single or double bond are excluded and the compound 3,7-dimethyl-1,6-octadiene-3-yl-acetate (linalyl acetate) of the formula (B)

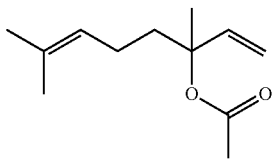

(B)

are excluded.

Another subject-matter of the invention is a method for preparing acetate compounds of the formula (I),

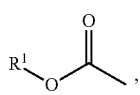

(I)

comprising the steps of c) providing at least one compound of the formula (II)

(II)

d) reacting the compound of the formula (II) with a ketene of the formula (III)

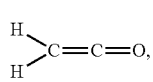

(III)

to obtain compounds of the formula (I), where $R^1$ is a heteroatom-free $C_8$-$C_{12}$-hydrocarbon radical, with the proviso that the compounds 1-acetoxymethyl-1,2,2,6-tetramethylcyclohexane and compounds of the formula (A)

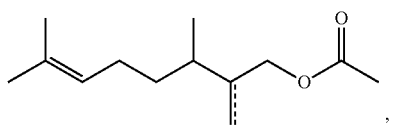

(A)

where ═ is a single or double bond are excluded.

A first preferred embodiment is a method for preparing acetate compounds of the formula (Ia)

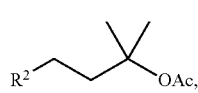

(Ia)

where $R^2$ is an unsubstituted $C_5$-$C_8$-cycloalkyl or unsubstituted $C_6$-$C_{10}$-aryl, especially cyclohexyl or phenyl.

A second preferred embodiment is a method for preparing acetate compounds of the formula (Ib)

(Ib)

where $R^3$ is a cyclohexyl substituted by $C_2$-$C_4$-alkyl and/or $C_2$-$C_4$-alkenyl, particularly preferably 2-isopropyl-5-methylcyclohexyl or 2-isopropenyl-5-methylcyclohexyl, specifically [(1R,2S,5R)-2-isopropyl-5-methylcyclohexyl], [(1S,2S,5R)-2-isopropyl-5-methylcyclohexyl] or [(1R,2S,5R)-2-isopropenyl-5-methylcyclohexyl].

A third preferred embodiment is a method for preparing acetate compounds of the formula (Ic)

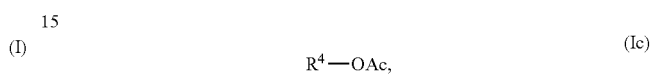

(Ic)

where $R^4$ is a branched $C_8$-$C_{10}$ alkenyl, preferably a branched $C_8$-$C_9$ alkenyl, especially 3,7-dimethylocta-2,6-dienyl.

DESCRIPTION OF THE INVENTION

Unless precisely specified otherwise below, the compound of the formula (I) refers to both cis/trans mixtures in any composition and the pure conformational isomers and also all diastereomers and optionally all enantiomers in pure form and also racemic and optically active mixtures of the enantiomers of these compounds.

If, in the following, cis and trans diastereomers of the compounds (I) are in question, only one of the enantiomeric forms is shown in each case.

If the configuration of the stereocentres is not explicitly stated, all isomers are included in each case.

In the context of the invention, the prefix $C_n$-$C_m$ indicates the number of carbon atoms which a molecule to which it refers or a radical to which it refers may have.

In the context of the present invention, the expression $C_8$-$C_{12}$-hydrocarbon radical represents linear or branched, optionally substituted alkyl, linear or branched, optionally substituted alkenyl, optionally substituted cycloalkyl or optionally substituted aryl, where the number of carbon atoms is 8 to 12.

In the context of the present invention, the expression $C_1$-$C_{12}$-alkyl groups and $C_8$-$C_{12}$-alkyl groups each represents linear and branched optionally substituted alkyl groups.

Suitable $C_8$-$C_{12}$-alkyl groups are preferably selected from n-octyl, 2-ethylhexyl, n-nonyl, n-decyl, n-undecyl, n-dodecyl and constitutional isomers thereof.

Suitable $C_1$-$C_7$-alkyl groups are in each case unbranched and branched, saturated, optionally substituted hydrocarbon radicals having 1 to 7 carbon atoms, wherein preference is given to $C_1$-$C_6$-alkyl groups, especially $C_1$-$C_4$-alkyl groups. $C_1$-$C_6$-alkyls are, for example, methyl, ethyl, n-propyl, isopropyl, n-butyl, isobutyl (2-methylpropyl), secbutyl (1-methylpropyl), tert-butyl (1,1-dimethylethyl), n-pentyl, n-hexyl, n-heptyl and the constitutional isomers thereof.

In the context of the present invention, the expression $C_2$-$C_{12}$-alkenyl groups and $C_8$-$C_{12}$-alkenyl groups each represents linear and branched, optionally substituted alkenyl groups having in each case 1, 2, 3 or more than 3 C—C double bonds.

Suitable $C_8$-$C_{12}$-alkenyl groups are preferably selected from n-octenyl, n-octadienyl, n-octatrienyl, n-nonenyl, n-nonadienyl, n-nonatrienyl, n-decenyl, n-decadienyl, n-decatrienyl, n-undecenyl, n-undecadienyl, n-undecatrienyl, n-dodecenyl, n-dodecadienyl, n-dodecatrienyl and constitutional isomers thereof.

Suitable $C_2$-$C_6$-alkenyl groups, preferably $C_2$-$C_4$-alkenyl, are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, n-pentenyl, n-pentadienyl, n-hexenyl, n-hexadienyl, n-hexatrienyl and constitutional isomers thereof.

In the context of the invention, cycloalkyl refers to a cycloaliphatic radical preferably having 3 to 10, particularly preferably 5 to 8 carbon atoms. Examples of cycloalkyl groups are, particularly, cyclopropyl, cyclobutyl, cyclopentyl, cyclohexyl, cycloheptyl or cyclooctyl. Cycloalkyl is especially cyclohexyl.

Substituted cycloalkyl groups may have one or more substituents (e.g. 1, 2, 3, 4 or 5) depending on the size of the ring. These are each preferably independently selected from $C_1$-$C_6$-alkyl and $C_1$-$C_6$-alkoxy. In the case of substitution, the cycloalkyl groups preferably bear one or more, for example one, two, three, four or five $C_1$-$C_6$-alkyl groups. Examples of substituted cycloalkyl groups are particularly 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-isobutylcyclohexyl and 2-, 3- and 4-tert-butylcyclohexyl.

In the context of the present invention, the expression "aryl" includes mono- or polycyclic aromatic hydrocarbon radicals typically having 6 to 10 carbon atoms. Examples of aryl are especially phenyl, naphthyl, indenyl and specifically phenyl.

Substituted aryls may have one or more substituents (e.g. 1, 2, 3, 4 or 5) depending on the number and size of their ring systems. These are each preferably independently selected from $C_1$-$C_6$-alkyl and $C_1$-$C_6$-alkoxy. Examples of substituted aryl radicals are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-disec-butylphenyl, 2,4,6-tri-sec-butylphenyl, 2-, 3- and 4-tert-butylphenyl.

In the context of the invention, catalysts are understood as at least one zinc salt, which may also be present as a hydrate or polyhydrate.

Particular preference is given to using a zinc salt of a carboxylic acid as a catalyst, especially a monocarboxylic acid having 1 to 18 carbon atoms or dicarboxylic acid having 2 to 18 carbon atoms. These include, e.g. zinc formate, zinc acetate, zinc propionate, zinc butyrate, zinc stearate, zinc succinate or zinc oxalate. Particular preference is given to zinc acetate.

The suitable and preferred conditions stated below for the preparation of compounds of the general formula (I) with a ketene (III) apply equally to the preparation of a compound of the general formula (I.a), (I.b) or (I.c) with the ketene (III), unless otherwise stated.

In the compounds of the formula (I) and (II), $R^1$ is preferably a straight-chain or branched $C_8$-$C_{12}$-alkyl, straight-chain or branched $C_8$-$C_{12}$-alkenyl; $C_5$-$C_8$-cycloalkyl, unsubstituted or substituted by $C_1$-$C_4$-alkyl and/or $C_2$-$C_4$-alkenyl; $C_5$-$C_8$-cycloalkyl-$C_1$-$C_6$-alkyl, unsubstituted or substituted by $C_1$-$C_4$-alkyl; $C_6$-$C_{10}$-aryl-$C_1$-$C_6$-alkyl, unsubstituted or substituted by $C_1$-$C_4$-alkyl.

In the compounds of the formula (I) and (II), $R^1$ is particularly preferably a branched $C_8$-$C_{10}$ alkenyl, unsubstituted cyclohexyl-$C_2$-$C_6$-alkyl; $C_5$-$C_8$-cycloalkyl substituted by $C_1$-$C_4$-alkyl and/or $C_2$-$C_4$-alkenyl; or unsubstituted phenyl-$C_2$-$C_6$-alkyl.

In the compounds of the formula (I) and (II), $R^1$ is especially preferably 2-isopropyl-5-methylcyclohexyl, 2-isopropenyl-5-methylcyclohexyl, 2-methyl-4-phenylbutan-2-yl, 4-cyclohexyl-2-methylbutan-2-yl or 3,7-dimethylocta-2,6-dien-1-yl.

Specifically, in the compounds of the formula (I) and (II), $R^1$ is

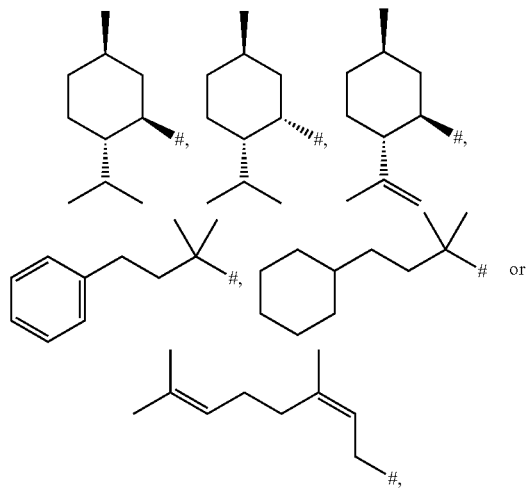

wherein # indicates the linkage to the remaining molecule radical of the formula (I) or (II).

Preference is given to subjecting the compounds of the general formula (II) to a reaction with a ketene (III) in the absence of an added catalyst.

A first preferred embodiment of the method according to the invention is a method for preparing compounds of the formula (Ia),

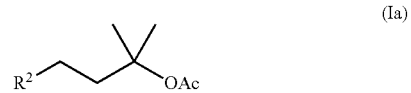

(Ia)

in which
(a) compounds of the formula (IIa)

(IIa)

are provided, where $R^2$ has the meaning defined above and in the following,
b) the compounds of the formula (IIa) are reacted with a ketene of the formula (III) to obtain compounds of the formula (Ia).

Step b) proceeds in accordance with the invention as described below. The reaction of compounds of the formula (IIa) to give compounds of the formula (Ia) proceeds analogously to the reaction of compounds of the formula (II) to give compounds of the formula (I).

A second preferred embodiment of the method according to the invention is a method for preparing compounds of the formula (Ib),

in which
(a) compounds of the formula (IIb)

are provided, where $R^3$ has the meaning defined above and in the following,
b) the compounds of the formula (IIb) are reacted with a ketene of the formula (III) to obtain compounds of the formula (Ib).

Step b) proceeds in accordance with the invention as described below. The reaction of compounds of the formula (IIb) to give compounds of the formula (Ib) proceeds analogously to the reaction of compounds of the formula (II) to give compounds of the formula (I).

A third preferred embodiment of the method according to the invention is a method for preparing compounds of the formula (Ic),

(a) compounds of the formula (IIc)

are provided, where $R^4$ has the meaning defined above and in the following,
b) the compounds of the formula (IIc) are reacted with a ketene of the formula (III) to obtain compounds of the formula (Ic).

Step b) proceeds in accordance with the invention as described below. The reaction of compounds of the formula (IIc) to give compounds of the formula (Ic) proceeds analogously to the reaction of compounds of the formula (II) to give compounds of the formula (I).

In the compounds (Ia) and (IIa), $R^2$ is preferably an unsubstituted $C_5$-$C_8$-cycloalkyl or an unsubstituted $C_6$-$C_{10}$-aryl.

In the compounds of the formula (Ia) and (IIa), $R^2$ is especially preferably cyclohexyl or phenyl.

In the compounds of the formula (Ib) and (IIb), $R^3$ is preferably cyclohexyl substituted by $C_1$-$C_4$-alkyl and/or $C_2$-$C_4$-alkenyl.

In the compounds of the formula (Ib) and (IIb), $R^3$ is especially preferably 2-isopropyl-5-methylcyclohexyl or 2-isopropenyl-5-methylcyclohexyl, specifically [(1R,2S, 5R)-2-isopropyl-5-methylcyclohexyl], [(1S,2S,5R)-2-isopropyl-5-methylcyclohexyl] or [(1R,2S,5R)-2-isopropenyl-5-methylcyclohexyl].

In the compounds of the formula (Ic) and (IIc), $R^4$ is preferably a branched $C_8$-$C_{10}$-alkenyl.

In the compounds of the formula (Ic) and (IIc), $R^4$ is especially preferably a branched $C_8$-$C_9$-alkenyl, particularly 3,7-dimethylocta-2,6-dienyl.

Alcohols of the general formula (II) suitable for use in the method according to the invention, especially (IIa), (IIb) or (IIc) in step a), and methods for the preparation thereof, are known in principle to those skilled in the art. Detailed synthetic routes for preparing the alcohol component are described, for example, in EP 17177666.9 and PCT/EP2017/069637.

Ketene of the formula (III) $CH_2$=C=O (ethenone) is employed for use in the method according to the invention.

The ketene (III) is preferably generated by high temperature pyrolysis of acetone or acetic acid at temperatures generally higher than 650° C. The temperature for generating the ketene (III) is preferably in a range from 650 to 1000° C., particularly preferably from 700 to 900° C.

In a specific embodiment, the ketene (III) is prepared under reduced pressure. The pressure is preferably in a range from about 100 to 900 mbar, particularly preferably from 300 to 500 mbar, especially from 350 to 450 mbar. In an alternative embodiment, the ketene (III) is prepared at ambient pressure ("unpressurized"). In this case, the pressure is preferably in a range from about 950 to 1050 mbar.

Since the ketene compound (III) is an exceptionally reactive compound which has a strong tendency to dimerize forming diketenes, a ketene compound is used in the method according to the invention which has preferably been prepared only briefly beforehand. The method according to the invention is rendered particularly advantageous when using ketene (III) which has been prepared directly prior to the reaction in the method according to the invention, for example, by thermal cleavage of acetone, acetic acid or acetic anhydride or by dehydrochlorination of acetyl chloride using bases such as triethylamine.

In a first variant of the method according to the invention, the ketene (III) is introduced into the reaction mixture below the liquid surface such that it sparges the reaction mixture. The ketene is advantageously fed into the reaction mixture under intensive stirring so that no ketene substantially converts into the gas phase in relatively large amounts.

The pressure of the ketene (III) must be sufficiently high in order to overcome the hydrostatic pressure of the reaction mixture above the ketene input, optionally supported by a stream of inert gas, e.g. nitrogen.

The ketene (III) can be introduced via any suitable devices. Good distribution and rapid mixing are important here. Suitable devices are, for example, sparging lances which may be fixed in position or preferably nozzles. The nozzles can be provided at or near the bottom of the reactor. For this purpose, the nozzles may be configured as openings from a hollow chamber surrounding the reactor. However, preference is given to using immersed nozzles with suitable feed lines. A plurality of nozzles can, for example, be arranged in the form of a ring. The nozzles may point upward or downward. The nozzles preferably point obliquely downward.

In a second variant of the method according to the invention, the ketene (III) is prepared under reduced pressure and reacted under reduced pressure with at least one alcohol compound of the general formula (II), preferably of the formula (IIa), (IIb) or (IIc). The pressure during the preparation and reaction of the ketene (III) is preferably in a range from about 100 to 900 mbar, particularly preferably from 300 to 500 mbar, especially from 350 to 450 mbar.

Methods and devices for preparing ethenone are described, for example, in Organic Syntheses, Coll. Vol. 1, p. 330 (1941) and Vol. 4, p. 39 (1925) and in the Chemiker Zeitung [The Chemists Journal] 97, No. 2, pages 67 to 73 (1979).

An excess of the ketene compound (III) can lead to undesired side reactions. Therefore, the reaction of the compound of the general formula (II) with the ketene (III) is preferably carried out using at most equimolar amounts of the ketene compound (III).

The alcohol compound of the general formula (II), preferably of the formula (IIa), (IIb) or (IIc), is preferably reacted with the ketene compound (III) in such a way that an accumulation of the ketene compound in the reaction mixture is avoided at all times in the reaction.

The reaction of the compound of the general formula (II) with the ketene (III) preferably takes place in such a way that ketene is introduced into the reaction mixture until the compound (II) is essentially completely reacted. "Essentially reacted" is here understood to mean a conversion of at least 98%, preferably at least 99%.

The compound of the general formula (II) is preferably subjected to a reaction with a ketene (III) at a temperature in the range of 0 to 150° C., preferably from 10 to 120° C.

In a first preferred embodiment, the compound of the general formula (II), preferably compounds (IIa), (IIb) or (IIc), is subjected to a reaction with a ketene (III) in the absence of an added catalyst.

In a preferred embodiment, the alcohol used is a primary alcohol. Very particular preference is given to subjecting compounds (IIc) to a reaction with a ketene (III) in the absence of an added catalyst.

In a further preferred embodiment, the alcohol used is a secondary alcohol. Very particular preference is given to subjecting compounds (IIb) to a reaction with a ketene (III) in the absence of an added catalyst.

In a further preferred embodiment, the alcohol used is a tertiary alcohol. Preference is given to subjecting compounds (IIa) to a reaction with a ketene (III) in the absence of an added catalyst.

It is also possible to subject the compound of the general formula (II) to a reaction with a ketene (III) in the presence of an added catalyst.

In one embodiment, the compound of the general formula (II) is subjected to a reaction with a ketene (III) in the presence of an added catalyst. The alcohol used is preferably a tertiary alcohol. Preference is given to subjecting compounds (IIa) to a reaction with a ketene (III) in the presence of an added catalyst. Preference is given to using at least one zinc salt as catalyst which may also be present as a hydrate or polyhydrate.

Particular preference is given to using a zinc salt of a carboxylic acid as catalyst, especially a monocarboxylic acid having 1 to 18 carbon atoms or dicarboxylic acid having 2 to 18 carbon atoms. These include, e.g. zinc formate, zinc acetate, zinc propionate, zinc butyrate, zinc stearate, zinc succinate or zinc oxalate. Particular preference is given to zinc acetate.

It is very advantageous in the method according to the invention that the catalysts generally only have to be used in very small amounts, which makes the method more cost-effective and facilitates the work-up of the reaction mixture. This applies in particular to using a zinc salt as catalyst.

The catalyst is preferably used in an amount of 0.01 to 2% by weight, particularly preferably 0.02 to 0.5% by weight, based on the total amount of the compound (II) (or (II.a)).

Step b) is preferably carried out directly undiluted, i.e. without additional solvent. In one case, the alcohol compound (II) liquid at room temperature is initially charged and reacted with the ketene compound (III). In another case, a melt of an alcohol compound (II) solid at room temperature is initially charged and reacted with the ketene compound (III). Moreover, step b) may be carried out in a solvent which is inert to the ketene compound (III). Suitable solvents are hydrocarbons, for example toluene, or esters, for example ethyl acetate, and particularly also the respective corresponding acetate compound (III) as long as this is liquid.

To perform the reaction according to the invention, it is advantageous to proceed in such a way that said reaction is carried out in a suitable reaction vessel comprising, as essential components, a good stirring and/or mixing device, a metering device for ketene, a heating device to start the reaction and to maintain the reaction temperature during the postreaction, a cooling device to remove the heat of reaction of the exothermic reaction and a vacuum pump.

For an optimal reaction regime, it is advantageous to meter in the ketene such that it is never present in excess in the reaction mixture and that the reaction mixture is always thoroughly mixed.

For an optimal reaction regime, it is further advantageous to avoid too rapid addition of ketene and also to clearly establish the end of the reaction, spectroscopically for example, or by the declining exothermicity of the esterification or the detection of ketene at the reactor outlet possibly serving as criteria.

It is possible to detect ketene, for example, by IR spectroscopy by means of the characteristic carbonyl vibration.

By means of the method according to the invention, it is possible to prepare the compounds of the general formula (I), especially compounds of the formula (Ia), (Ib) or (Ic), in high purities and nevertheless in excellent yields and space-time yields by reaction with ketene of the formula (III) in a technically simple manner. Since the reactants are essentially completely converted to products, the method according to the invention is characterized by a maximum atom economy.

The acetate compounds obtainable by the method according to the invention are particularly advantageously suitable as fragrances or for providing a fragrance.

The specific embodiment 1 is about a method for preparing acetate compounds of the formula (I),

comprising the steps of
e) providing at least one compound of the formula (II)

f) reacting the compound of the formula (II) with a ketene of the formula (III)

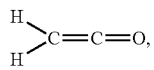

(III)

to obtain compounds of the formula (I),
where $R^1$ is a heteroatom-free $C_8$-$C_{12}$-hydrocarbon radical, with the proviso that the compounds 1-acetoxymethyl-1,2,2,6-tetramethylcyclohexane and compounds of the formula (A)

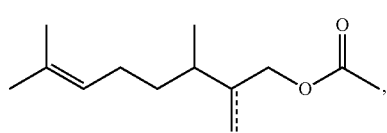

(A)

where ≈ is a single or double bond, are excluded.

In a specific embodiment 1', the method of embodiment 1 does not serve to prepare the compound 3,7-dimethyl-1,6-octadiene-3-yl-acetate (linalyl acetate) of the formula (B)

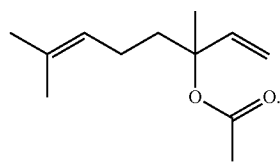

(B)

The specific embodiment 2 is about a method according to embodiment 1, wherein the compound of the general formula (II) is subjected to a reaction with a ketene (III) in the absence of an added catalyst.

The specific embodiment 3 is about a method according to one of the preceding embodiments 1 or 2, where $R^1$ is a straight-chain or branched $C_8$-$C_{12}$-alkyl, straight-chain or branched $C_8$-$C_{12}$-alkenyl; $C_5$-$C_8$-cycloalkyl, unsubstituted or substituted by $C_1$-$C_4$-alkyl and/or $C_2$-$C_4$-alkenyl; $C_5$-$C_8$-cycloalkyl-$C_1$-$C_6$-alkyl, unsubstituted or substituted by $C_1$-$C_4$-alkyl; $C_6$-$C_{10}$-aryl-$C_1$-$C_6$-alkyl, unsubstituted or substituted by $C_1$-$C_4$-alkyl.

The specific embodiment 4 is about a method according to one of the preceding embodiments 1 to 3, where $R^1$ is a branched $C_8$-$C_{10}$ alkenyl, unsubstituted cyclohexyl-$C_2$-$C_6$-alkyl, $C_5$-$C_8$-cycloalkyl, substituted with $C_1$-$C_4$-alkyl and/or $C_2$-$C_4$-alkenyl, or unsubstituted phenyl-$C_2$-$C_6$-alkyl.

The specific embodiment 5 is about a method according to one of the preceding embodiments 1 to 4, where $R^1$ is

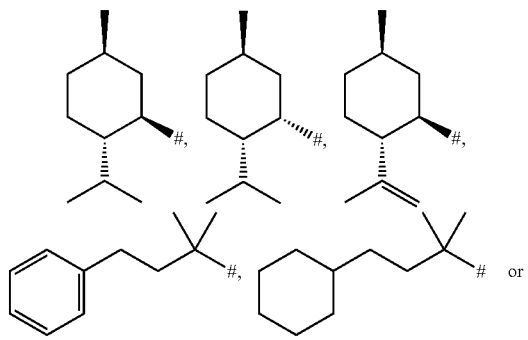

-continued

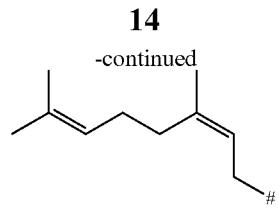

wherein # indicates the linkage to the remaining molecule radical of the formula (I) or (II).

The specific embodiment 6 is about a method according to one of the preceding embodiments 1 to 5 to produce acetate compounds of the formula (Ia)

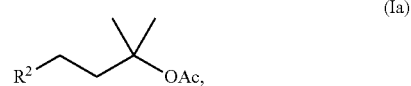

(Ia)

where $R^2$ is an unsubstituted $C_5$-$C_8$-cycloalkyl or an unsubstituted $C_6$-$C_{10}$-aryl, in particular cyclohexyl or phenyl.

The specific embodiment 7 is about a method according to one of the embodiments 1-5 for preparing acetate compounds of the formular (Ib)

(Ib)

where $R^3$ is a cyclohexyl substituted by $C_1$-$C_4$-alkyl and/or $C_2$-$C_4$-alkenyl, particularly preferably 2-isopropyl-5-methylcyclohexyl or 2-isopropenyl-5-methylcyclohexyl, specifically [(1R,2S,5R)-2-isopropyl-5-methylcyclohexyl], [(1S,2S,5R)-2-isopropyl-5-methylcyclohexyl] or [(1R,2S,5R)-2-isopropenyl-5-methylcyclohexyl].

The specific embodiment 8 is about a method according to one of the preceding embodiments 1 to 5 for preparing acetate compounds of the formula (Ic)

(Ic)

where $R^4$ is a branched $C_8$-$C_{10}$ alkenyl, preferably a branched $C_8$-$C_9$ alkenyl, especially 3,7-dimethylocta-2,6-dienyl.

The specific embodiment 9 is about a method according to one of the embodiments 1 to 5 and 7 to 8, where the compounds of the general formula (Ib) or (Ic) are subjected to a reaction with a ketene (III) in the absence of an added catalyst.

The specific embodiment 10 is about a method according to one of the embodiments 1, 1' and 3 to 6, where the compound of the general formula (Ia) is subjected to a reaction with a ketene (III) in the presence of an added catalyst.

The specific embodiment 11 is about a method according to one of the preceding embodiments 1 to 10, where the compound of the general formula (II) is subjected to a reaction with a ketene (III) at a temperature ranging from 0 to 150° C., preferably from 10 to 120° C., particularly preferably from 40 to 110° C. The examples which follow serve to illustrate the invention, but without restricting it in any way.

EXAMPLES

The following chemicals and abbreviations were used:
2-Methyl-4-cyclohexyl butan-2-ol
2-Methyl-4-phenylbutan-2-ol
Menthol
Menthyl acetate
Neomenthol: 2-isopropyl-5-methylcyclohexanol
Isopulegol: 2-isopropenyl-5-methylcyclohexanol
Nerol: 2,6-dimethyl-2,6-octadien-8-ol
Ketene: ethenone ($H_2C=C=O$)

Platinum-cobalt color numbers were determined according to the method of DIN EN ISO 6271-2 at 50 mm layer thickness and are on a scale of 0 to 500.

The respective alcohols were initially charged either without solvent (if the alcohol itself was liquid) or as a melt, or in the solvent specified in each case. Ketene was obtained by pyrolysis of acetone at ca. 700° C. and the pyrolysis gas stream was passed through the reaction mixture with vigorous stirring at the stated temperature until the conversion was complete.

Example 1:
2-Acetoxy-2-methyl-4-cyclohexylbutane

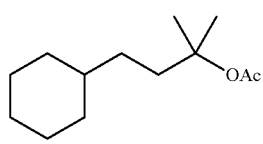

2-Methyl-4-cyclohexylbutan-2-ol (119.9 g; 0.70 mol) was initially charged at 60° C. and reacted with ketene as described above. Conversion was complete after 14.5 h. The product was purified by fractional distillation (124.8 g; 84%).

Example 2: 2-Acetoxy-2-methyl-4-phenylbutane

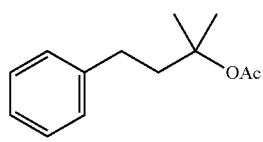

2-Methyl-4-phenylbutan-2-ol (137.6 g; 0.84 mol) was initially charged as a melt at 60° C. (melting point: 24-25° C.) and reacted with ketene as described above. Conversion was complete after 20.5 h. The product was purified by fractional distillation (143.5 g; 83%).

Example 3: (L)-Menthyl Acetate

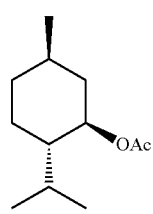

Menthol (57.4 g; 0.37 mol) was dissolved in menthyl acetate (57.4 g; 0.29 mol) and reacted with ketene at 90° C. as described above. Conversion was complete after 6 h and the crude product already comprised 99% by weight menthyl acetate by GC. If required, the product may be further purified by fractional distillation (yield 82% based on menthol used).

The color of the crude product is colorless. The platinum-cobalt color number of the crude product is less than 30. Prior aqueous extraction is not necessary.

Alternatively, menthol may be initially charged as a melt at 90° C. (melting point 41-44° C.). The reaction with ketene is carried out in an analogous manner.

Example 4: (D)-Neomenthyl Acetate

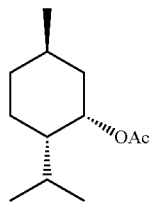

Neomenthol (57.5 g; 0.37 mol) was initially charged at 80° C. and reacted with ketene as described above. Conversion was complete after 5 h and the product was purified by fractional distillation (50.0 g; 68%).

Example 5: (L)-Isopulegyl Acetate

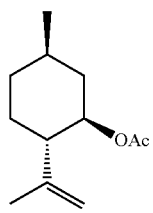

Isopulegol (54.3 g; 0.35 mol) was initially charged at 80° C. and reacted with ketene as described above. Conversion was complete after 4.5 h and the product was purified by fractional distillation (48.8 g; 71%).

Example 6: Neryl Acetate

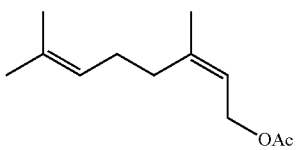

Nerol (107.9 g; 0.70 mol) was initially charged at 60° C. and reacted with ketene as described above. Conversion was complete after 15.5 h. The product was purified by fractional distillation (113.1 g; 82%).

The invention claimed is:

1. A method for preparing acetate compounds of the formula (I),

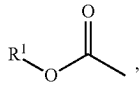
(I)

comprising the steps of
 a) providing at least one compound of the formula (II)

R¹—OH   (II)

b) reacting the compound of the formula (II) with a ketene of the formula (III)

(III)

to obtain compounds of the formula (I),
 where R¹ is a heteroatom-free $C_5$-$C_{12}$-hydrocarbon radical, with the proviso that the compounds 1-acetoxymethyl-1,2,2,6-tetramethylcyclohexane and compounds of the formula (A)

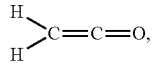
(A)

where ~~~ is a single or double bond, are excluded, wherein the compound of the general formula (II) is subjected to a reaction with a ketene (III) in the absence of an added catalyst.

2. The method according to claim 1, where R¹ is a straight-chain or branched $C_8$-$C_{12}$-alkyl, straight-chain or branched $C_8$-$C_{12}$-alkenyl; $C_5$-$C_8$-cycloalkyl, unsubstituted or substituted by $C_1$-$C_4$-alkyl and/or $C_2$-$C_4$-alkenyl; $C_5$-$C_8$-cycloalkyl-$C_1$-$C_6$-alkyl, unsubstituted or substituted by $C_1$-$C_4$-alkyl; $C_6$-$C_{10}$-aryl-$C_1$-$C_6$-alkyl, unsubstituted or substituted by $C_1$-$C_4$-alkyl.

3. The method according to claim 1, where R¹ is a branched $C_8$-$C_{10}$ alkenyl, unsubstituted cyclohexyl-$C_2$-$C_6$-alkyl; $C_5$-$C_8$-cycloalkyl substituted by $C_1$-$C_4$-alkyl and/or $C_2$-$C_4$-alkenyl; or unsubstituted phenyl-$C_2$-$C_6$-alkyl.

4. The method according to claim 1, where R¹ is

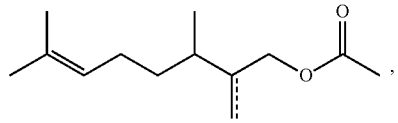

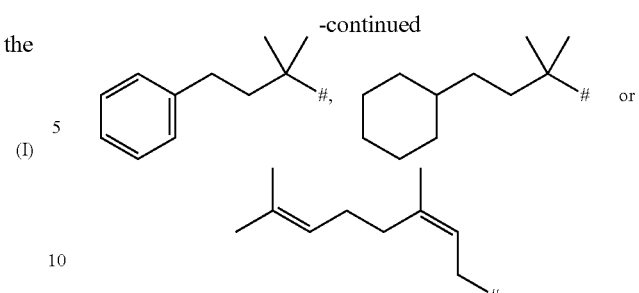

wherein # indicates the linkage to the remaining molecule radical of the formula (I) or (II).

5. The method according to claim 1 for preparing acetate compounds of the formula (Ia)

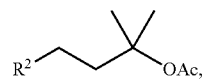
(Ia)

where R² is an unsubstituted $C_5$-$C_8$-cycloalkyl or unsubstituted $C_6$-$C_{10}$-aryl.

6. The method according to claim 1 for preparing acetate compounds of the formula (Ib)

R³—OAc,   (Ib)

where R³ is a cyclohexyl substituted by $C_1$-$C_4$-alkyl and/or $C_2$-$C_4$-alkenyl.

7. The method according to claim 1 for preparing acetate compounds of the formula (Ic)

R⁴—OAc,   (Ic)

where R⁴ is a branched $C_8$-$C_{10}$ alkenyl.

8. The method according to claim 1, wherein the compounds of the general formula (IIb)

R³—OH   (IIb)

wherein R³ is a cyclohexyl substituted by $C_1$-$C_4$ alkyl and/or $C_2$-$C_4$-alkenyl,
 or (IIc)

R⁴—OH   (IIc)

wherein R⁴ is a branched $C_8$-$C_{10}$ alkenyl,
 are subjected to a reaction with a ketene (III) in the absence of an added catalyst.

9. The method according to claim 1, wherein the compound of the general formula (IIa)

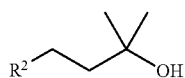
(IIa)

wherein R² is an unsubstituted $C_5$-$C_8$-cycloalkyl or unsubstituted $C_6$-$C_{10}$-aryl,
is subjected to a reaction with a ketene (III) in the absence of an added catalyst.

10. The method according to claim 1, wherein the compound of the general formula (II) is subjected to a reaction with a ketene (III) at a temperature in the range of 0 to 150° C.

11. The method according to claim 1 for preparing acetate compounds of the formula (Ic)

$$R^4\text{—OAc,} \quad (Ic)$$

where R⁴ is a branched $C_8$-$C_9$ alkenyl.

12. The method according to claim 1 for preparing acetate compounds of the formula (Ic)

$$R^4\text{—OAc,} \quad (Ic)$$

where R⁴ is 3,7-dimethylocta-2,6-dienyl.

13. The method according to claim 1, wherein the compound of the general formula (II) is subjected to a reaction with a ketene (III) at a temperature in the range of 10 to 120° C.

14. The method according to claim 1, wherein the compound of the general formula (II) is subjected to a reaction with a ketene (III) at a temperature in the range of 40 to 110° C.

15. The method according to claim 1 for preparing acetate compounds of the formula (Ia)

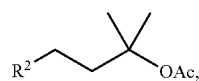
(Ia)

where R² is an cyclohexyl or phenyl.

16. The method according to claim 1 for preparing acetate compounds of the formula (Ib)

$$R^3\text{—OAc,} \quad (Ib)$$

where R³ is 2-isopropyl-5-methylcyclohexyl or 2-isopropenyl-5-methylcyclohexyl.

17. The method according to claim 1 for preparing acetate compounds of the formula (Ib)

$$R^3\text{—OAc,} \quad (Ib)$$

where R³ is [(1R,2S,5R)-2-isopropyl-5-methylcyclohexyl], [(1S,2S,5R)-2-isopropyl-5-methylcyclohexyl] or [(1R,2S,5R)-2-isopropenyl-5-methylcyclohexyl].

* * * * *